United States Patent [19]
Serra-Tosio et al.

[11] Patent Number: 5,902,936
[45] Date of Patent: May 11, 1999

[54] COMPRESSION TEST DEVICE FOR PAPER STRIPS

[75] Inventors: Jean-Marie Serra-Tosio, Meylan; Yves Chave, Gieres, both of France

[73] Assignee: Association de Gestion de l'Ecole, Paris, France

[21] Appl. No.: 09/062,306

[22] Filed: Apr. 17, 1998

[30] Foreign Application Priority Data

Apr. 21, 1997 [FR] France ................................. 97/05097

[51] Int. Cl.⁶ ............................................. G01N 3/20
[52] U.S. Cl. ............................ 73/851; 73/159; 73/838; 73/849
[58] Field of Search ............................ 73/159, 790, 818, 73/821, 823, 825, 838, 840, 849, 851; 116/212

[56] References Cited

U.S. PATENT DOCUMENTS

| | | | |
|---|---|---|---|
| 1,385,164 | 7/1921 | Witham, Jr. ............................ | 73/849 X |
| 2,645,937 | 7/1953 | Skalmusky et al. ...................... | 73/821 |
| 2,647,397 | 8/1953 | Dietert .................................. | 73/821 X |
| 2,864,253 | 12/1958 | Lenton .................................. | 73/825 |
| 3,566,680 | 3/1971 | Dankoff et al. ......................... | 73/851 |
| 3,593,573 | 7/1971 | Ely ...................................... | 73/825 X |
| 3,608,367 | 9/1971 | Karol ................................... | 73/825 |
| 3,906,782 | 9/1975 | Early et al. ........................... | 73/821 X |
| 3,914,993 | 10/1975 | Babcock ................................. | 73/821 |
| 4,393,716 | 7/1983 | Clark et al. ............................ | 73/818 |
| 4,938,071 | 7/1990 | Kobayashi et al. ..................... | 73/849 |
| 5,048,347 | 9/1991 | Knowles ................................ | 73/821 |
| 5,528,942 | 6/1996 | Baratta ................................. | 73/818 X |
| 5,641,912 | 6/1997 | Manahan, Sr. ........................ | 73/825 X |
| 5,717,144 | 2/1998 | Dunaway ............................... | 73/821 X |

FOREIGN PATENT DOCUMENTS 1810786  4/1993  U.S.S.R. .

*Primary Examiner*—Elizabeth L. Dougherty
*Attorney, Agent, or Firm*—Arthur L. Plevy

[57] ABSTRACT

The present invention relates to a compression test device for a paper strip, including means for laterally holding the strip to limit its buckling during the testing. The lateral holding means include a tube in which the strip is freely rolled with more than one turn.

11 Claims, 2 Drawing Sheets

COMPRESSION TEST DEVICE FOR PAPER STRIPS

BACKGROUND OF THE INVENTION

1. Field of the Invention

The present invention relates to paper compression rupture tests. Such tests are, for example, used for classifying papers according to their ability to form cardboard boxes for packing. Packing cardboard boxes, which are to be piled up, must have a good compression resistance.

2. Discussion of the Related Art

FIG. 1 illustrates a so-called "ring-crush" standardized compression test, which is described, for example, in "Physical and Mechanical Testing of Paper and Paperboard", volume 1, Richard E. Mark editor, 1983. A paper strip to be tested 10 is curved to form a ring. The ring is maintained in a groove of a bearing 12. The width of strip 10, its protrusion with respect to bearing 12, and the ring diameter are standardized (respectively, 12.6 mm, 6.3 mm and 47 mm). Further, strip 10 is wound substantially in one turn to form the ring.

During the test, ring 10 is crushed at constant speed by a plate parallel to bearing 12. The result of the test is the maximum force exerted during the crushing.

The results of this test are much lower than the pure compression resistance since, despite the low profile of ring 10, its walls tend to locally buckle. Thus, the results rather translate the resistance to local buckling than the compression resistance, especially for thin papers.

Further, this type of testing, due to the low height of the ring, does not enable rheological tests, that is, to acquire the curve of the compression deformation according to the force.

FIGS. 2 and 3 illustrate two compression tests which provide a more accurate evaluation of the resistance to pure compression and enable a rheology. These tests are also described in the above-mentioned document.

In FIG. 2, a paper strip 14 is grasped at each end by a respective jaw 16, 17. Between the jaws, strip 14 is guided between two plates 19, 20 which are meant to enable strip 14 to slide while preventing its buckling when jaws 16 and 17 are brought close to each other to perform the test.

A disadvantage of this system is that the setting of the spacing between plates 19 and 20 is delicate. On the one hand, they must not be too spaced apart from each other, which would cause, as is shown, undulations of the strip, due to the buckling. On the other hand, they must not be too close to each other, since strip 14 would be submitted to a strong friction during its deformation. In one case as in the other, the measures would be distorted.

For this reason, the system of FIG. 3 is preferred, where each of guide plates 19 and 20 has been replaced with a series of flexible thin plates 22 perpendicular to the plane of strip 14. Such a system enables a firm lateral holding of strip 14, while this strip can deform freely in compression between jaws 16, 17, the deformations being allowed relatively freely thanks to the flexibility of thin plates 22.

To reduce the buckling risk of strip 14 between two successive thin strips 22, the number of thin strips is multiplied, which increases the complexity and the cost of the system, without however totally suppressing the buckling risk. Further, if the number of thin plates 22 is multiplied, their resilience has a non-negligible influence upon the measure results.

SUMMARY OF THE INVENTION

An object of the present invention is to provide a compression test device for paper strips which is of particularly simple structure while providing results close to reality.

This object is achieved by means of a compression test device including a tube in which the strip is freely rolled with more than one turn.

According to an embodiment of the present invention, the height of the tube is smaller than the height of the rolled strip.

According to an embodiment of the present invention, the lateral holding means include two spaced apart tubes, each flush with one end of the rolled strip.

According to an eimbodiment of the present invention, both tubes include complementary shapes in axial sliding cooperation.

According to an embodiment of the present invention, the device includes a jack mounted to compress the rolled strip between an element integral with the jack cylinder and a plate attached to a first end of the jack piston.

According to an embodiment of the present invention, said element and the plate include shoulders for centering the tubes.

According to an embodiment of the present invention, the device includes a displacement sensor cooperating with the second end of the jack piston.

According to an embodiment of the present invention, the tubes are perforated, so that the strip is homogeneously submitted to the surrounding atmosphere.

The foregoing objects, features and advantages of the present invention will be discussed in detail in the following non-limiting description of specific embodiments in connection with the accompanying drawings.

DETAILED DESCRIPTION

According to the present invention, paper strips of sufficient height to ensure an adequate rheological test are tested in compression. The strips are rolled to form several turns of small diameter with respect to the height. A tubular sample of small diameter is thus formed. The diameter is, for example, in the order of 15 mm.

The local buckling tendency of the walls of a tube appears to decrease with the diameter, while the global buckling risk of the tube increases. To prevent the global buckling of the tubular sample, the present invention provides to insert this sample in a relatively rigid guiding tube.

The strip is freely rolled from a flat position. It thus naturally tends to unroll and to press against the internal walls of the guiding tube. It is useless to provide an internal guiding. Further, the effort of the strip against the tube is particularly low, causing negligible friction which does not affect the measures.

Figure 4B:
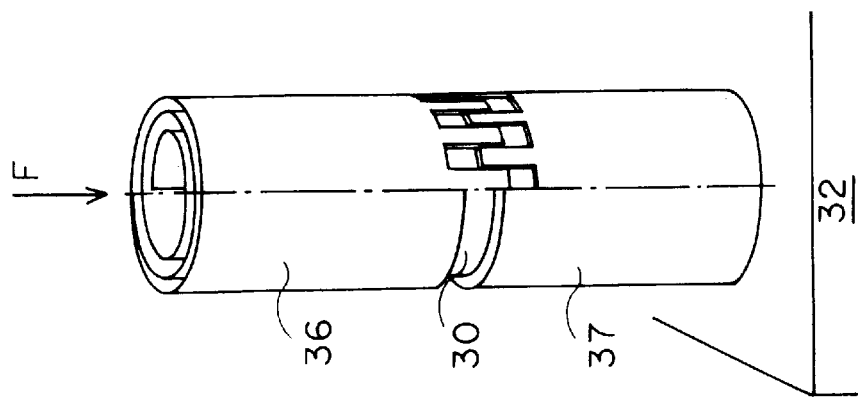
FIGS. 4A and 4B illustrate two implementations of a paper strip compression test according to the present invention.
Figure 4A:
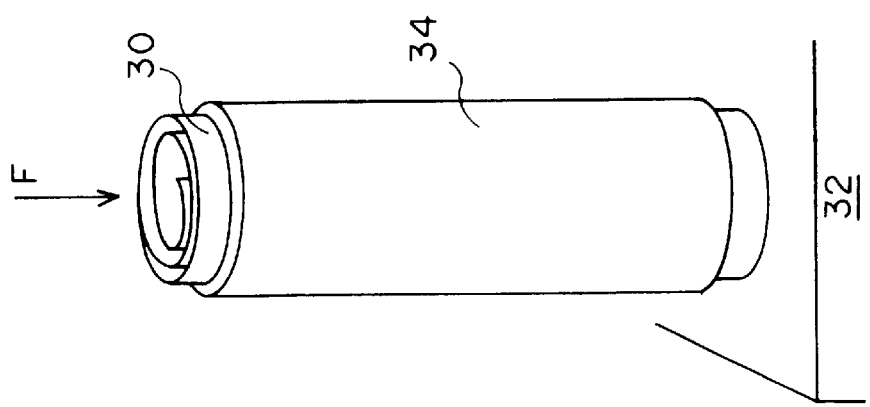

In FIGS. 4A and 4B, a rolled paper strip 30 is placed upright on a bearing 32 and is compressed in the direction of an arrow F by a plate (not shown) parallel to bearing 32.

In FIG. 4A, a single guide tube 34 is provided. Tube 34 has a lower height than rolled strip 30, so that tube 34 does not disturb the free compression of rolled strip 30. The height difference, shown with exaggeration in the drawings, is just sufficient for rolled strip 30 to reach its compression rupture point.

This difference ranges between 1 and 4 mm according to the height of the rolled strip and to its rigidity, which represents a eight causing low buckling risks.

FIG. 4B shows a solution to avoid edge phenomena which could occur if the method illustrated in FIG. 4A is applied. Here, two guide tubes 36 and 37 of same internal diameter are used. Tubes 36 and 37 are flush, each, with one of the ends of rolled strip 30, and leave a sufficient central clearance to enable the rolled strip to freely compress to its rupture point.

As shown in the left-hand portion of FIG. 4B, the space between tubes 36 and 37 may be ring-shaped. Preferably, as shown in the right-hand portion of FIG. 4B, tubes 36 and 37 have complementary shapes in axial sliding cooperation, for example notches. This solution reduces the buckling risks.

According to an embodiment not shown, the height of the single guide tube is greater than that of rolled strip 30, this rolled strip 30 being compressed by a piston which slides inside the tube. In this case, no portion of the rolled strip is preferentially submitted to buckling.

The testing can be performed totally conventionally. For example, rolled strip 30 is compressed at constant speed while the compression force is measured.

To obtain results close to reality, the number of turns of strip 30 should be relatively high. An optimum value is obtained when the cross-section area of the rolled strip is substantially equal to half the cross-section area of the opening of the guiding tubes.

Figure 1:
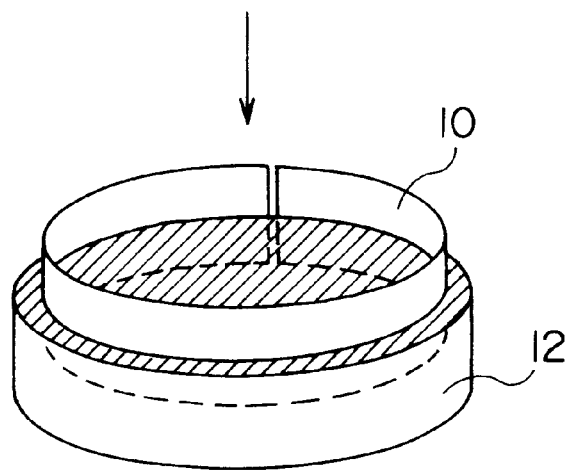
FIGS. 1 to 3, previously described, illustrate different conventional paper strip compression tests.
Figure 2:
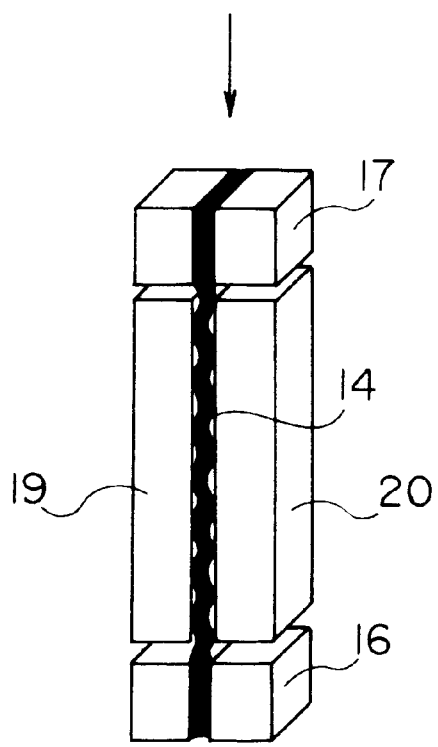
Figure 3:
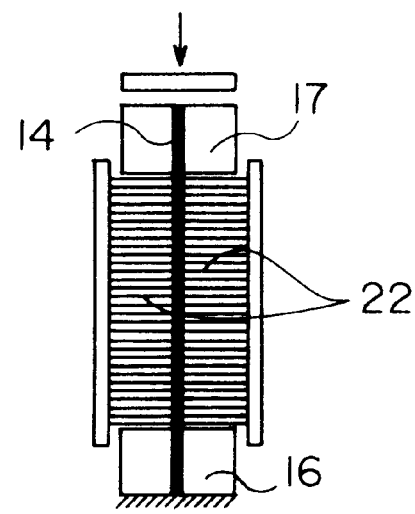
Figure 5:
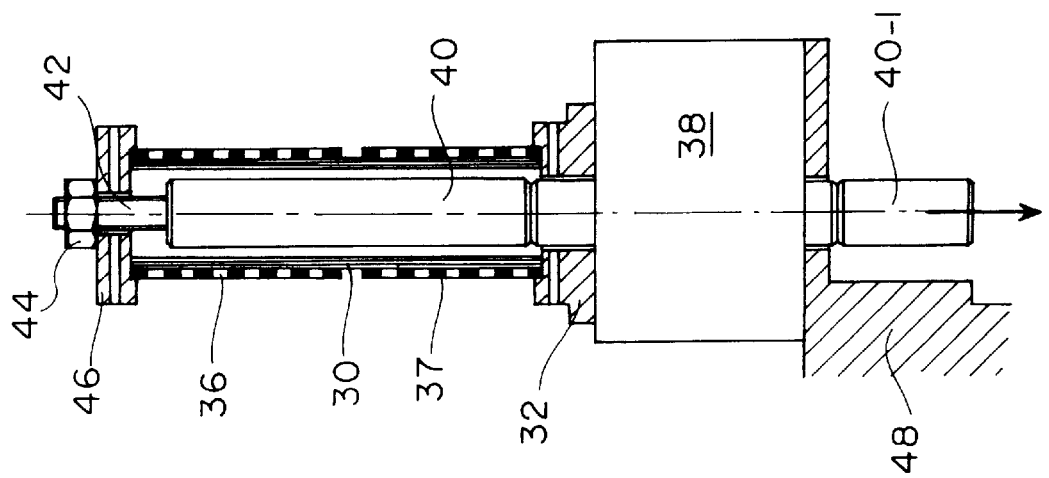
FIG. 5 shows an example of a practical embodiment of a test device according to the present invention.

FIG. 5 illustrates an example of a compression test device according to the present invention. This device uses, as an example, two guiding tubes 36 and 37. Bearing 32 on which rolled strip 30 is placed is formed by the cylinder of a single stroke jack 38, the piston 40 of which extends upwards inside rolled strip 30. Preferably, jack 38 has no return spring for piston 40.

The diameter of piston 40 is smaller than the inner diameter of rolled strip 30. The upper end of piston 40 is provided with a threading 42 on which is screwed a nut 44 to make a plate 46 bear against the upper end of rolled strip 30. Piston 40 is coupled to a displacement sensor. Preferably, as shown, plate 46 and bearing 32 are provided with shoulders for maintaining tubes 36 and 37 centered, which avoids any risk of relative shifting of the tubes during the compression.

With such a system, several possibilities are available to perform the testing. A first possibility consists of servo-controlling the pressure of jack 38 to obtain a constant speed displacement of piston 40. Another possibility consists of increasing the pressure of jack 38 by successive steps and measuring the corresponding displacements of piston 40. The system also enables a constant compression force to be applied and the deformation in time to be measured (flow measurement).

A device of the type of FIG. 5 may advantageously be assembled, with several similar devices, on a removable frame 48 meant to equip a measurement apparatus of the type described in European patent application 0508914 incorporated herein by reference. This device enables to submit several samples (rolled strips 30) to a controlled atmosphere and to automate the displacement measurements.

To adapt the device of FIG. 5 to this device, piston 40 of jack 38 extends from both ends of the cylinder, that is, it comprises an end 40-1 extending downwards from the cylinder of jack 38. The elements necessary for the displacement measurement will be attached to this end 40-1.

If it is effectively desired to measure the behavior of the samples according to the atmosphere, guiding tubes 36, 37 are preferably perforated as shown, so that the atmosphere may contact the external surface of rolled strip 30. Further, for the atmosphere to come into contact with the internal surface of strip 30, plate 46 and bearing 32 are perforated, as shown.

If the displacement measures are performed at the level of lower end 40-1 of the jack piston, the expansion of this piston inside rolled strip 30 under the effort of the jack should be compensated. This expansion is proportional to the force exerted by the jack and may easily be compensated by computation in the measurement system.

Of course, the present invention is likely to have various alterations, modifications, and improvements which will readily occur to those skilled in the art. Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A compression test device for a paper strip (30), including means (34, 36, 37) for laterally holding the strip to limit buckling during testing, which means include a tube in which the strip is freely rolled with more than one turn.

2. The test device of claim 1, wherein the height of the tube (34) is smaller than the height of the rolled strip (30).

3. The test device of claim 1, wherein the lateral holding means include two spaced apart tubes (36, 37), each flush with one end of the rolled strip.

4. The test device of claim 3, wherein both tubes include complementary shapes in axial sliding cooperation.

5. The test device of any of claim 1, including a jack (38) mounted to compress the rolled strip between an element (32) integral with a jack cylinder (38) and a plate (46) attached to a first end of a jack piston (40).

6. The test device of claim 5, wherein said element (32) and the plate (46) include shoulders for centering the tube.

7. The test device of claim 5, including a displacement sensor cooperating with a second end (40-1) of the jack piston.

8. The test device of any of claim 1, wherein the tube is perforated, so that the strip is homogeneously submitted to the surrounding atmosphere.

9. The test device of claim 2 including a jack (38) mounted to compress the rolled strip between an element (32) integral with a jack cylinder (38) and a plate (46) attached to a first end of a jack piston (40).

10. The test device of claim 3 including a jack (38) mounted to compress the rolled strip between an element (32) integral with a jack cylinder (38) and a plate (46) attached to a first end of a jack piston (40).

11. The test device of claim 4 including a jack (38) mounted to compress the rolled strip between an element (32) integral with a jack cylinder (38) and a plate (46) attached to a first end of a jack piston (40).

* * * * *